(12) United States Patent
Riehl et al.

(10) Patent No.: US 8,600,893 B2
(45) Date of Patent: *Dec. 3, 2013

(54) SYSTEM AND METHOD FOR BACK OFFICE PROCESSING OF BANKING TRANSACTIONS USING ELECTRONIC FILES

(71) Applicant: JPMorgan Chase Bank, N.A., New York, NY (US)

(72) Inventors: Louis Riehl, Marlboro, NJ (US); George Anderson, Freehold, NJ (US)

(73) Assignee: JPMorgan Chase Bank, National Association, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/737,981

(22) Filed: Jan. 10, 2013

(65) Prior Publication Data

US 2013/0124419 A1 May 16, 2013

Related U.S. Application Data

(63) Continuation of application No. 11/281,436, filed on Nov. 18, 2005, now Pat. No. 8,370,232, which is a continuation of application No. 09/413,971, filed on Oct. 7, 1999, now Pat. No. 7,062,456.

(60) Provisional application No. 60/119,284, filed on Feb. 9, 1999.

(51) Int. Cl.
| | |
|---|---|
| *G06Q 40/00* | (2012.01) |
| *G06Q 40/02* | (2012.01) |
| *G06F 19/20* | (2011.01) |
| *G06K 5/00* | (2006.01) |
| *G06Q 20/18* | (2012.01) |
| *G06Q 20/40* | (2012.01) |

(52) U.S. Cl.
CPC ............... *G06Q 40/00* (2013.01); *G06Q 40/02* (2013.01); *G06Q 20/18* (2013.01); *G06Q 20/40* (2013.01); *G06F 19/20* (2013.01); *G06K 5/00* (2013.01)
USPC .................. 705/45; 705/35; 705/42; 235/379; 235/380; 235/381

(58) Field of Classification Search
CPC ....... G06Q 40/00; G06Q 40/02; G06Q 20/18; G06Q 20/40; G06F 19/20; G06F 17/24; G06K 5/00
USPC .................. 705/30, 39, 42, 45; 235/379–381; 715/210
See application file for complete search history.

(56) References Cited

U.S. PATENT DOCUMENTS

| | | | |
|---|---|---|---|
| 3,872,448 A | | 3/1975 | Mitchell, Jr. |
| 4,417,136 A | | 11/1983 | Rushby et al. |
| 4,523,330 A | | 6/1985 | Cain |
| 4,617,457 A | | 10/1986 | Granzow et al. |
| 5,040,227 A | * | 8/1991 | Lyke et al. .................. 382/138 |
| 5,159,687 A | | 10/1992 | Richburg |
| 5,168,444 A | | 12/1992 | Cukor et al. |
| 5,175,682 A | * | 12/1992 | Higashiyama et al. ......... 705/45 |
| 5,237,159 A | | 8/1993 | Stephens et al. |
| 5,278,982 A | | 1/1994 | Daniels et al. |
| 5,313,616 A | | 5/1994 | Cline et al. |
| 5,321,238 A | * | 6/1994 | Kamata et al. ................. 705/45 |
| 5,347,518 A | | 9/1994 | Lee |
| 5,455,946 A | | 10/1995 | Mohan et al. |
| 5,630,173 A | | 5/1997 | Oprescu |
| 5,701,471 A | | 12/1997 | Subramanyam |
| 5,703,344 A | * | 12/1997 | Bezy et al. ..................... 235/379 |
| 5,748,878 A | | 5/1998 | Rees et al. |
| 5,752,034 A | | 5/1998 | Srivastava |
| 5,758,061 A | | 5/1998 | Plum |
| 5,764,972 A | | 6/1998 | Crouse et al. |
| 5,774,553 A | | 6/1998 | Rosen |
| 5,784,557 A | | 7/1998 | Oprescu |
| 5,787,402 A | | 7/1998 | Potter et al. |
| 5,794,218 A | * | 8/1998 | Jennings et al. ................ 705/35 |
| 5,819,236 A | | 10/1998 | Josephson |
| 5,828,883 A | | 10/1998 | Hall |
| 5,832,463 A | * | 11/1998 | Funk .............................. 705/35 |
| 5,832,523 A | | 11/1998 | Kanai et al. |
| 5,835,770 A | | 11/1998 | Shum et al. |
| 5,845,293 A | | 12/1998 | Veghte et al. |
| 5,872,976 A | | 2/1999 | Yee et al. |
| 5,907,846 A | | 5/1999 | Berner et al. |

| | | | |
|---|---|---|---|
| 5,920,719 A | 7/1999 | Sutton et al. | |
| 5,940,844 A * | 8/1999 | Cahill et al. | 715/268 |
| 5,978,477 A | 11/1999 | Hull et al. | |
| 6,009,405 A | 12/1999 | Leymann et al. | |
| 6,012,087 A | 1/2000 | Freivald et al. | |
| 6,014,671 A | 1/2000 | Castelli et al. | |
| 6,026,237 A | 2/2000 | Berry et al. | |
| 6,029,002 A | 2/2000 | Afifi et al. | |
| 6,058,393 A | 5/2000 | Meier et al. | |
| 6,065,009 A | 5/2000 | Leymann et al. | |
| 6,081,808 A | 6/2000 | Blackman et al. | |
| 6,108,698 A | 8/2000 | Tenev et al. | |
| 6,125,390 A | 9/2000 | Touboul | |
| 6,128,602 A * | 10/2000 | Northington et al. | 705/35 |
| 6,138,112 A | 10/2000 | Slutz | |
| 6,145,121 A | 11/2000 | Levy et al. | |
| 6,163,776 A | 12/2000 | Periwal | |
| 6,188,400 B1 | 2/2001 | House et al. | |
| 6,226,652 B1 | 5/2001 | Percival et al. | |
| 6,237,143 B1 | 5/2001 | Fontana et al. | |
| 6,243,862 B1 | 6/2001 | Lebow | |
| 6,256,635 B1 | 7/2001 | Arrouye et al. | |
| 6,263,121 B1 | 7/2001 | Melen et al. | |
| 6,266,683 B1 | 7/2001 | Yehuda et al. | |
| 6,269,479 B1 | 7/2001 | Puram | |
| 6,279,008 B1 | 8/2001 | Tung Ng et al. | |
| 6,301,701 B1 | 10/2001 | Walker et al. | |
| 6,311,320 B1 | 10/2001 | Jibbe | |
| 6,311,327 B1 | 10/2001 | O'Brien et al. | |
| 6,334,117 B1 * | 12/2001 | Covert et al. | 705/43 |
| 6,336,122 B1 | 1/2002 | Lee et al. | |
| 6,356,920 B1 | 3/2002 | Vandersluis | |
| 6,381,609 B1 | 4/2002 | Breitbart et al. | |
| 6,385,618 B1 | 5/2002 | Ng et al. | |
| 6,397,221 B1 | 5/2002 | Greef et al. | |
| 6,405,209 B2 | 6/2002 | Obendorf | |
| 6,411,957 B1 | 6/2002 | Dijkstra | |
| 6,418,446 B1 | 7/2002 | Lection et al. | |
| 6,418,448 B1 | 7/2002 | Sarkar | |
| 6,418,451 B1 | 7/2002 | Maimone | |
| 6,446,099 B1 | 9/2002 | Peairs | |
| 6,449,623 B1 | 9/2002 | Bohannon et al. | |
| 6,453,310 B1 | 9/2002 | Zander | |
| 6,456,995 B1 | 9/2002 | Salo et al. | |
| 6,467,052 B1 | 10/2002 | Kaler et al. | |
| 6,477,540 B1 | 11/2002 | Singh et al. | |
| 6,490,581 B1 | 12/2002 | Neshatfar et al. | |
| 6,502,095 B2 | 12/2002 | Breitbart et al. | |
| 6,502,104 B2 | 12/2002 | Fung et al. | |
| 6,532,467 B1 | 3/2003 | Brocklebank et al. | |
| 6,535,894 B1 | 3/2003 | Schmidt et al. | |
| 6,539,337 B1 | 3/2003 | Provan et al. | |
| 6,539,383 B2 | 3/2003 | Charlet et al. | |
| 6,539,397 B1 | 3/2003 | Doan et al. | |
| 6,539,398 B1 | 3/2003 | Hannan et al. | |
| 6,557,039 B1 | 4/2003 | Leong et al. | |
| 6,571,249 B1 | 5/2003 | Garrecht et al. | |
| 6,574,640 B1 | 6/2003 | Stahl | |
| 6,578,129 B1 | 6/2003 | da Silva Junior et al. | |
| 6,591,260 B1 | 7/2003 | Schwarzhoff et al. | |
| 6,601,075 B1 | 7/2003 | Huang et al. | |
| 6,651,076 B1 | 11/2003 | Asano | |
| 6,665,086 B2 | 12/2003 | Hull et al. | |
| 6,678,705 B1 | 1/2004 | Berchtold et al. | |
| 6,681,380 B1 | 1/2004 | Britton et al. | |
| 6,691,139 B2 | 2/2004 | Ganesh et al. | |
| 6,697,835 B1 | 2/2004 | Hanson et al. | |
| 6,701,514 B1 | 3/2004 | Haswell et al. | |
| 6,711,594 B2 | 3/2004 | Yano et al. | |
| 6,714,219 B2 | 3/2004 | Lindhorst et al. | |
| 6,763,384 B1 | 7/2004 | Gupta et al. | |
| 6,796,488 B1 * | 9/2004 | Saffarian | 235/379 |
| 6,880,010 B1 | 4/2005 | Webb et al. | |
| 6,918,013 B2 | 7/2005 | Jacobs et al. | |
| 6,938,072 B2 | 8/2005 | Berman et al. | |
| 2002/0007287 A1 | 1/2002 | Straube et al. | |
| 2002/0029228 A1 | 3/2002 | Rodriguez et al. | |
| 2002/0038226 A1 | 3/2002 | Tyus | |
| 2002/0038320 A1 | 3/2002 | Brook | |
| 2002/0049666 A1 | 4/2002 | Reuter et al. | |
| 2002/0065695 A1 | 5/2002 | Francoeur et al. | |
| 2002/0083034 A1 | 6/2002 | Orbanes et al. | |
| 2002/0091702 A1 | 7/2002 | Mullins | |
| 2002/0116205 A1 | 8/2002 | Ankireddipally et al. | |
| 2002/0143774 A1 | 10/2002 | Vandersluis | |
| 2002/0144101 A1 | 10/2002 | Wang et al. | |
| 2002/0178439 A1 | 11/2002 | Rich et al. | |
| 2002/0188765 A1 | 12/2002 | Fong et al. | |
| 2003/0014421 A1 | 1/2003 | Jung | |
| 2003/0018666 A1 | 1/2003 | Chen et al. | |
| 2003/0027561 A1 | 2/2003 | Iyer | |
| 2003/0046313 A1 | 3/2003 | Leung et al. | |
| 2003/0050931 A1 | 3/2003 | Harman et al. | |
| 2003/0069975 A1 | 4/2003 | Abjanic et al. | |
| 2003/0070158 A1 | 4/2003 | Lucas et al. | |
| 2003/0088593 A1 | 5/2003 | Stickler | |
| 2003/0126151 A1 | 7/2003 | Jung | |
| 2003/0131007 A1 | 7/2003 | Schirmer et al. | |
| 2003/0140045 A1 | 7/2003 | Heninger et al. | |
| 2003/0140308 A1 | 7/2003 | Murthy et al. | |
| 2003/0145047 A1 | 7/2003 | Upton | |
| 2003/0163603 A1 | 8/2003 | Fry et al. | |
| 2003/0167266 A1 | 9/2003 | Saldanha et al. | |
| 2003/0167445 A1 | 9/2003 | Su et al. | |
| 2003/0177118 A1 | 9/2003 | Moon et al. | |
| 2003/0177341 A1 | 9/2003 | Devillers | |
| 2003/0191849 A1 | 10/2003 | Leong et al. | |
| 2003/0217033 A1 | 11/2003 | Sandler et al. | |
| 2003/0217083 A1 | 11/2003 | Taylor | |
| 2004/0122872 A1 | 6/2004 | Pandya et al. | |
| 2005/0027658 A1 | 2/2005 | Moore et al. | |
| 2005/0060345 A1 | 3/2005 | Doddington | |
| 2005/0065987 A1 | 3/2005 | Telkowski et al. | |

FOREIGN PATENT DOCUMENTS

| | | |
|---|---|---|
| EP | 04466342 A2 | 2/1991 |
| WO | WO 95/03586 | 2/1995 |
| WO | WO 96/34350 | 10/1996 |
| WO | WO 02/46980 | 6/2002 |

OTHER PUBLICATIONS

Glassman, Cathy C.; "Is Image everything?"; Independent Banker, v47, n2; Feb. 1997; pp. 1-2.*

POS News; "California Sets the New Network Interchange Pace"; Mar. 3, 1995; pp. 1-6.*

Anonymous: "Deterring check fraud: the model positive pay services agreement and commentary"; Business Lawyer, v. 54, n2; Feb. 1999; pp. 1-24.

Britt, Phil: "check imaging technology"; American's Community Banker, v. 7, n1; Jan. 1998; pp. 1-5.

Taubert, Christy: "Workflow system rids branches of paper"; Bank System & Technology, v.33, n6; Jun. 1996; p. 1.

American Banker: "Reengineering: Chase takes a leadership role in electronic checking: a move to save the industry $2 billion to $3 billion a year"; Jun. 9, 1997; pp. 1-2.

Glassman, Cathy C.: "Is image everything?"; Independent Banker, v47, n2; Feb. 1997: pp. 1-3.

"Comment: Banks must evolve to nurture fitness to survive"; American Banker, vol. 163, No. 79; Apr. 28, 1998; pp. 1-4.

"Comment: Time to overhaul deposit processing systems"; American Banker, vol. 163, No. 235: Dec. 10, 1998; pp. 1-4.

"Reengineering update: Item processing offers best opportunity for improved efficiency"; American Banker, vol. 159, No. 78; Apr. 25, 1994; pp. 1-3.

Duggan, 2.40 General—Reviews and Abstracts, SPI Database of Software Technologies, p. 1-5, Feb. 1, 1974.

Hellerstein, A Generalized Search Tree for Database Systems, Jan. 19, 1996.

Deng et al., A Probabilistic Approach to fault Diagnosis in Linear Lighwaves Network, Department of Electrical Engineering, May 1992, pp. 1-122.

Sammet, Beginning of 4.6 Software Evaluation, Tests and Measurements and RMF I/O Time Validation, Association of Computing Machinery, p. 519.

Xu, ERDraw: An XML-based ER-diagram Drawing and Translation Tool.
Vanbommel, Genetic Algorithms for Optimal Logical Database Design Information and Software Technology, vol. 36, No. 12, p. 725-732, 1994.
Strom et al., Gryphon: An Information Flow Based Approach to Message Brokering, International Symposium on software Reliability, Jun. 20, 2005.
Hilbert, Hilbert, et al., An Approach to Large Scale Collection of Application Usage Data Over the Internet, Software Engineering 1998, Proceedings of the 1998 International Conference, Abstract, Apr. 1998.
Chen et al., Improving Index Performance through Prefetching School of Computer Science Carnegie Mellon University, Dec. 2000.
Van Steen et al., Model for Worldwide Tracking of Distributed Objects, VRIJE Universiteit, Amsterdam.
Quantitative Monitoring of Software Development by Time-Based and Intercheckpoint Monitoring, Software Engineering Journal, vol. 5, Iss. 1, p. 43-49, Abstract, Jan. 1990.
Moser, Transactions in a Distributed Object Environment, Department of Electrical and Computer Engineering, Jun. 19, 2005.
Ramakrishnan, Tree-Structured Indexes Module 2, Lectures 3 and 4.

\* cited by examiner

*Primary Examiner* — Ella Colbert

(74) *Attorney, Agent, or Firm* — Goodwin Procter LLP

(57) ABSTRACT

As banking transactions are processed by a bank teller, all of the relevant information with respect to the transaction (e.g., dollar amount) is captured in an electronic file. Each of the electronic files from the various branches of the bank are forwarded to a central back office processing center where the electronic files are combined into a single Transaction Repository. At the end of the branch day, all of the paper associated with the transactions is forwarded from the branches to the back office processing center. The paper transactions are imaged in the conventional manner and the Magnetic Ink Character Recognition (MICR) data is read from the paper. The present invention then automatically correlates the images and MICR data captured from the paper with the complete transaction record contained in the Transaction Repository. Most of the conventional back office processing can now be performed without the need to perform character recognition and without the need for excess human intervention.

35 Claims, 12 Drawing Sheets

SYSTEM AND METHOD FOR BACK OFFICE PROCESSING OF BANKING TRANSACTIONS USING ELECTRONIC FILES

This application is a continuation of U.S. patent application Ser. No. 11/281,436, filed on Nov. 18, 2005, now U.S. Pat. No. 8,370,232, which is a continuation of U.S. patent application Ser. No. 09/413,971, filed on Oct. 7, 1999, now U.S. Pat. No. 7,062,456, which claims priority to Provisional application Ser. No. 60/119,284, filed on Feb. 9, 1999.

FIELD OF THE INVENTION

The present invention generally relates to systems and methods for back office processing of bank transactions and more particularly to a system and method which electronically captures transaction information at the time of execution of the transaction and uses this electronic information during the back office processing.

BACKGROUND OF THE INVENTION

Historically, a bank teller's interaction with customers and the bank's internal systems have been manually organized on a transaction by transaction basis with little to no capability of linking the information regarding the transaction with the paper(s) which constitute the transaction.

Some prior art teller systems maintained an electronic journal which allows the teller to perform limited research and allows the teller to reverse transactions selected from the electronic journal in the case where an error was actually discovered. However, this type of electronic journal is limited in its applicability as it is simply a sequential list of transactions performed at the bank. Furthermore, the electronic journal of the prior art has limited detail regarding transactions and must be supplemented by a continuous paper tape printed out at each teller system. Given the limited amount of information gathered at the teller workstation, the prior art methods and systems for back office processing were very labor and machine intensive. The term "back office" is well known to those skilled in the art and relates to the facility in the back which performs the processing for the bank, e.g. posting of transactions, clearing of checks, statement generation . . . Each branch of the bank forwards all of the documents (e.g., checks, deposits slips . . . ) to the back office at the end of the day for processing. Back office processing for banking transactions includes for example, posting of transactions, statement processing, proof of deposit processing, end of day confirmation, account reconciliation and archiving. Until recently, most of the capture of data from the paper representing the transactions (e.g., checks) was done manually at the back office. For example, an operator would physically look at the check and enter the dollar amount written on the check into a record in the bank's database used for tracking checks. As larger banks process huge volumes of checks, each operator in the back office was responsible for data entry for thousands of checks per day. The shear volume and repetitiveness of this process naturally led to errors in the data processing. Recently, systems have been developed which optically scan the financial documents data and use character recognition to capture the data previously captured by human operators (e.g., the amount written on a check). FIG. 1 illustrates such a prior art system and method of back office processing. Typically at the end of the day, each branch of the bank forwards all of the paper 10 associated with the day's transactions (e.g., checks, deposit slips . . . ) to a central location.

The first process undertaken at the back office is to capture both images of the paper (front and back) and the Magnetic Ink Character Recognition (MICR) data contained on the paper. Module 15, Check Processing Control System (CPCS) Prime Capture, accomplishes both of these functions using conventional image enabled sorters, optical readers and MICR readers. The image data of the two sides of each of the papers 10 is stored in an image archive database 20, while the MICR data read from the paper is stored in a CPCS database 25. Once the image and MICR data have been captured by the CPCS Prime Capture 15, a Character Recognition Engine 30 analyzes the captured images in order to determine the amount of the transaction. If the Character Recognition Engine 30 successfully reads the amount of the transaction, the amount is used to update the record for that transaction in the CPCS database 25. Typically the Character Recognition Engine 30 is able to interpret the amount on approximately 60% of the transactions with a 2% error rate.

If the MICRline data on the paper document is read incorrectly, in the MICRline Data Completion module 35, an operator looks at the image of the document and manually completes the MICRline data in the transaction record for the document. If the Character Recognition Engine 30 fails to capture the amount of the transaction, in the Amount Key Entry module an operator manually read the image of the check from the image database 20 and inputs the amount into the transaction record contained in the CPCS database. If the character recognition for the amount on a deposit slip does not reconcile with the sum of the amount character recognized from the checks included on the deposit slip, the transaction balanced in the Deposit Balancing 45 module.

In Deposit Balancing 45, the amount listed on a deposit slip is compared with the total of the amounts of the checks associated with the deposit slip. If these two totals match, the deposit is considered balanced. If the totals do not match, an operator has to manually review the images of the deposit slip and the associated checks in order to determine and correct the error. Errors could occur in any number of areas such as incorrect character recognition by the Character Recognition engine or incorrect human input in the Amount Key Entry process 40.

As described above, the conventional back office processing of financial documents from the branches of the bank are very labor intensive and error prone. Even with the above described automation aids, the process is still very labor and machine intensive and still produces errors which can only be resolved by human intervention.

SUMMARY OF THE INVENTION

In the present invention, as transactions are processed by a bank teller, the teller captures all of the relevant information with respect to the transaction for inclusion in an electronic file, the Electronic Journal. Each record in the Electronic Journal representing a transaction will contain at least the branch and teller identification, the type of transaction, any MICR data associated with the paper(s) constituting the transaction, and the amount, of the transaction. In a preferred embodiment of the present invention, the Electronic Journals from all of the branches are forwarded periodically throughout the day to a central location associated with the branches. In addition to the creation of the Electronic Journal, each branch, at the end of the day, forwards all the paper associated with the transactions to the back office processing center. In conjunction with this end of the day processing, each branch creates an electronic summary of transactions processed that day at the branch (end of day sums).

In a preferred embodiment, a single processing center performs all of the back office processing for all branches of the bank. Periodically throughout the day, this single back office accesses the Electronic Journals for all of the branches. Alternatively, the back office processing center could poll each of the branches independently to access the Electronic Journals.

After the importation of the Electronic Journal into the back office, all of the transaction records from the Electronic Journal are stored in a Transaction Repository memory. In parallel with this storage of the transaction records, a subset of the information contained in each of the transaction records is forwarded the back office module which performs the End of Day Confirmation process.

When the paper transactions arrive at the back office from the various branches, each of the paper transactions is imaged in the conventional manner and the MICR data is read from the paper. The back office can now automatically correlate the images and MICR data captured from the paper with the complete transaction record contained in the Transaction Repository. Since the transaction record already contains all of the information relevant to the transaction, the need to perform the character recognition, MICRline data completion and amount key entry performed in the prior art is eliminated (except in exception cases).

The present invention has numerous advantages over the prior art processing methods and systems including: a reduction of labor and equipment; a reduction in errors associated with the character recognition process; a reduction in the amount of character recognition and manual key entry which has to take place; simplification of the teller process due to far fewer sorts of physical paper; enabling of a more constant flow of work from the branches to the back office; extended customer hours for centralized Automated Teller Machines (ATM) and branch processing due to freed capacity at the back office; end of day proofing by tellers is all but eliminated; easy identification of missing papers; enhance the return items process for the bank; enable accurate assignment of the float for cashed checks; reduction of "on-us" financial control documents (e.g., General ledger tickets, Cash-in, Cash-out); and an improvement of the cash reconciliation process based upon earlier access to the document images.

BRIEF DESCRIPTION OF THE DRAWINGS

For the purposes of illustrating the present invention, there is shown in the drawings a form which is presently preferred, it being understood however, that the invention is not limited to the precise form shown by the drawing in which.

DETAILED DESCRIPTION OF THE INVENTION

Figure 2:
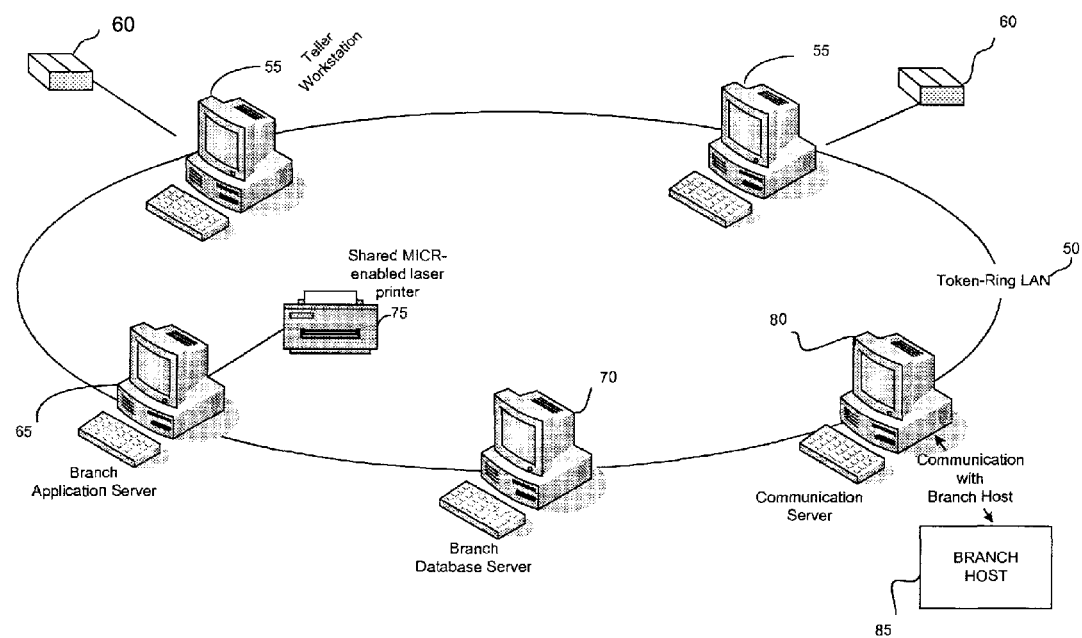
FIG. 2 depicts a typical hardware configuration at a branch location.

As described above, part of the present invention involves the teller capturing information concerning a transaction as the transaction is being processed by the teller. FIG. 2 illustrates a typical hardware configuration at a branch which includes a token ring network 50 of workstations. One of these networks 50 is established at each branch of the bank. Elements 55 represent workstations for use by the tellers in conducting transactions (e.g., at a teller window with a bank customer). Each teller workstation 55 also includes a MICR reader 60 which enables the teller to scan the MICR encoding on checks and other instruments.

Server 65 is an application server, while server 70 is a database server. Each of these servers 65, 70 provide common access to all of the applications and databases used at the branch. Through the network 50, each of the teller workstations 55 have access to the applications and databases residing on servers 65, 70. The application server 65 is shown as having a shared laser printer 75 connected thereto. Server 80 is a communication server which provides the connection between the network 50 and the branch host 85. As will be described below, transactions generated from the teller's workstations 55 are transmitted to the branch host 85 for confirmation processing.

A logical grouping of one or more consecutive transactions performed by a teller is known as a session. A customer session is one or more transactions performed for a single customer during the course of a single visit to the teller window. A non-customer session consists of one or more transactions performed by the teller without a customer being physically present at the teller's window.

As a teller initiates a session, a new record is opened in the Branch Electronic Journal which includes the number and date and start time of the session. The Branch Electronic Journal is, as implied by its name, a file which electronically records all of the actions (transaction processing) performed by the teller at the branch. Each session record in the Branch Electronic Journal includes the session ID and session start and end times and initial Session Balance (which may be zero), along with the Teller ID of the teller conducting the session and any customer ID obtained. Each transaction processed by the teller has a separate record entry within the session record in the Branch Electronic Journal.

Figure 4:
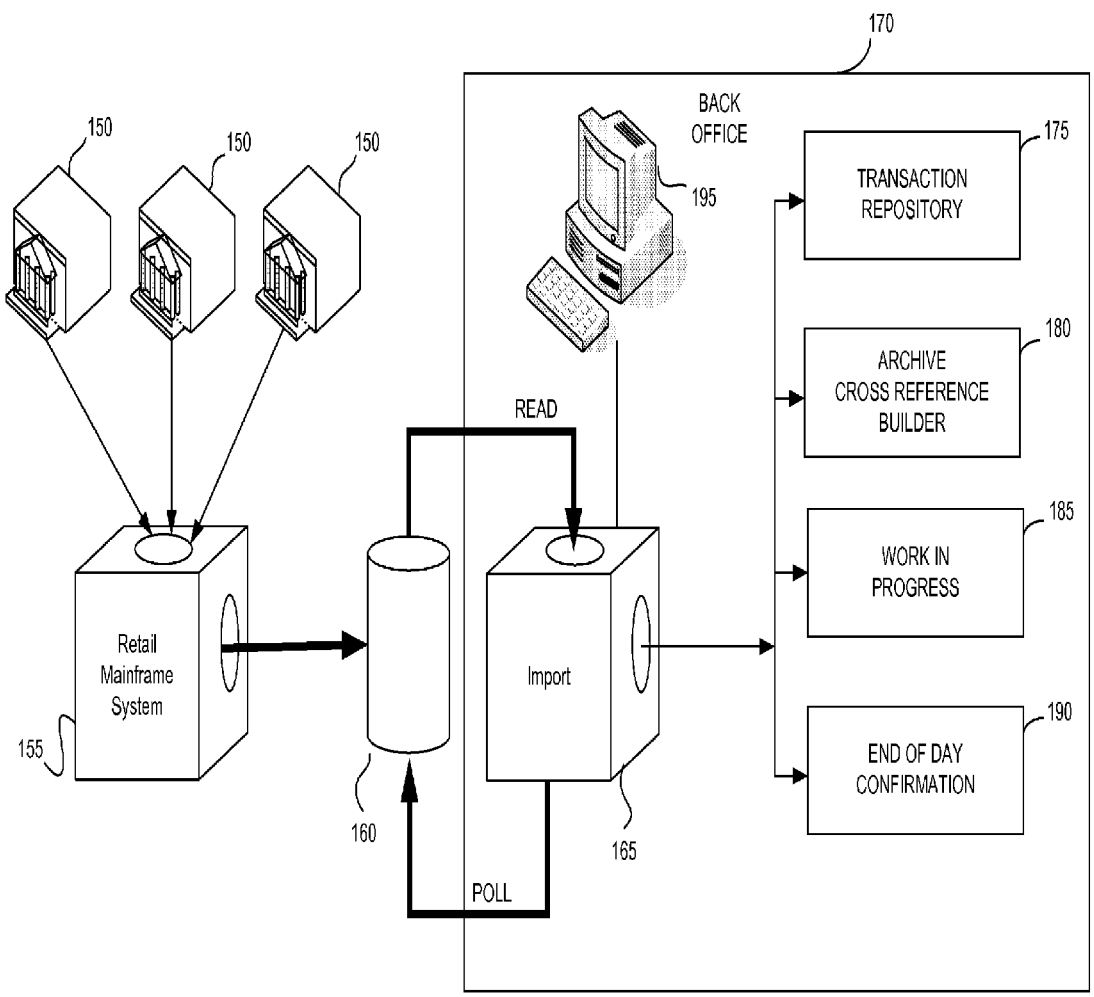
FIG. 4 is an overview of the system and the flow of data according to the present invention.

The transaction entry contains all pertinent details regarding the transaction including, for example: a transaction sequence number; the transaction type; account number; and the dollar amount. There are approximately two hundred and fifty different types of transactions which can be processed, but the back office is only concerned with approximately one hundred and thirty. FIG. 4 illustrates that in one embodiment of the present invention, the branches 150 only send the back office 170 transactions of the pertinent one hundred and thirty types. In an alternative embodiment, the branches 150 send records to the back office 170 related to all of the transactions conducted at the respective branches 150, regardless of type. In this embodiment, the back office 170 culls out only the types of transactions which require back office processing.

Each transaction is logged in the Branch Electronic Journal as it is sent to the branch host system 85 for confirmation. The transaction entries in the Branch Electronic Journal therefore reflect the "stream" order in which the transactions are sent to the branch host 85. The branch host response for each transaction is appended to the appropriate transaction entry as received, along with the time of receipt. The Branch Electronic Journal may be viewed and sorted selectively by the teller, but may not be edited or altered by any user, but may be selected by the teller for reversal. All teller activity is permanently recorded in the Branch Electronic Journal.

For each transaction which involves a piece of paper with a MICR code imprinted thereon (e.g., a check), the teller system prompts the teller to swipe the check(s) on reader 60 to capture the check information. The teller then individually enters the amount related to the paper (e.g., the amount of each check). This MICR data is appended to the transaction record in the Branch Electronic Journal.

Figure 3:
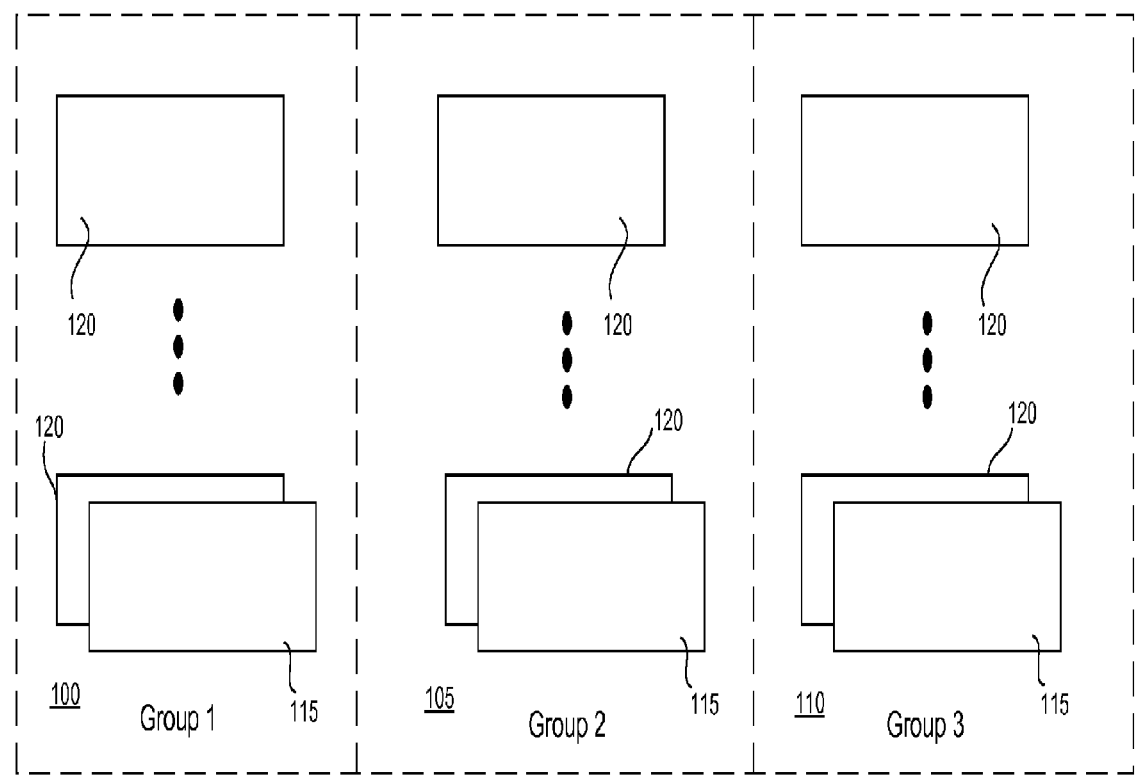
FIG. 3 illustrates the three groups of transactions which are generated at a branch.

As briefly described above, there are over two hundred and fifty different types of transactions which can be conducted at a branch. The back office processing is only concerned with approximately one hundred and thirty of these transactions. These one hundred and thirty transactions are logically and physically separated into three different groups. FIG. 3 illustrates the three different groupings, Group 1 (100), Group 2 (105) and Group 3 (110) of transactions generated at the various branches of the bank. The physical separation of the groups occurs at the teller's workstation when the transactions are processed. At the beginning of the day, or any point throughout the day, the teller generates three control tickets 115 which identify the group of transaction papers 120 which are physically grouped with the control ticket 115. As the teller processes transactions, the physical paper 120 associated with the transactions is separated into the one of the three groups defined by the control tickets 115. Periodically throughout the business day, and at least at the end of the branch day, all of the paper 115, 120 associated with the transactions processed by the branch, organized by the three groups, is shipped to the back office for processing as described below.

Group 1 (100) consists of credits and debits with cash, check or credit offsets and includes cash only deposits. The Group 1 (100) transactions are financially complete at the teller's window, and no further financial processing is required by the bank. The back office 170 requires the documentation with respect to these transactions for at least archival and research purposes. For cash only deposits, the MICR encoded deposit slip is the paper associated with the transaction. Group 2 (105) transactions are all deposits except cash only deposits and include check only, mixed, split and check deposits less cash. In processing Group 2 transactions, the teller swipes the deposit slip 120 in order to acquire the MICR data (e.g., the account and serial numbers). The teller further enters the cash amount (if any) and the total amount of the deposit. For each check in a Group 2 (105) deposit, the teller MICR swipes the check 120 and manually enters the dollar amount of the check. In a preferred embodiment of the present invention, the tellers only swipes and enters the amounts of Group 2 (105) checks 120 if the total number of checks involved in the transaction is below a threshold amount (e.g., less than five checks). If there are more checks 120 involved in the transaction than the threshold amount, the traditional back office processing described above is used to process the transaction at the back office.

Group 3 (110) transactions consist solely of checks 120, either cashed or used for payments (e.g., of a credit card balance) or sales (e.g., of travelers checks). As with checks 120 in Groups 1 and 2 (100, 105) checks 120 for Group 3 (110) are MICR swiped by the teller and the teller manually enters the dollar amount. As described above, all of the MICR data and the dollar amounts manually entered by the teller are input into record in the Branch Electronic Journal associated with the transaction. This is true for all transactions, whether they be Group 1, 2 or 3. Group 2 (105) and Group 3 (100) transactions are considered "live" even after they leave the branch 150 since the financial processing for the transaction is not yet complete (e.g., clearing of checks through the bank upon which the check is drawn).

FIG. 4 illustrates an overview of the system and the flow of data according to the present invention. As previously described, the various branches 150 of the bank forward their individual Branch Electronic Journals to a retail mainframe system 155 common to all of the branches 150. The forwarding of data is accomplished, for example, through a telecommunications line. Note that the term retail relates to the branch operations of the bank. Again, the Branch Electronic Journals contain records related to over two hundred and fifty different types of transactions and also contain other branch specific information which is of no interest to the back office. Accordingly, the retail mainframe 155 extracts only the information which is of interest to the back office (relating to approximately one hundred and thirty transactions) and generates a Transaction Journal file 160 which is for use by the back office.

As transaction records are received by the Retail mainframe 155 throughout the course of the day, the mainframe 155 builds the Transaction Journal 160. The process of building the Transaction Journal 160 is invoked at the start of each business day, and as described below passes certain transactions contained in the Transaction Journal 160 to the back office platform on a continuous basis throughout the day. As electronic transactions are received from branches 150 in the Branch Electronic Journals, the transactions are examined to determine if they are to be written to the Transaction Journal 160. By the end of the day, the Transaction Journal file 160 contains records for all of the relevant transactions performed at all of the branches 150 for the relevant time period (e.g., a day).

The following Transaction types are included in the Transaction Journal 160: Financial transactions (e.g., Group 2 (105) Deposit Tickets and associated checks, and Group 3 (110) Payment, Sale, or Cashed Checks that have been MICR Swiped by the Teller); Archive Only transactions (e.g., Group 1 (100) transactions); Work In Progress Batch (Groups 1, 2, and 3) transactions; Branch Confirmation transactions; and All Items Only transactions (e.g., non paper transactions). The relevancy of these different types of record will be discussed below with respect to the back office processing.

The records contained in the Transaction Journal 160 preferably include the following fields: Financial Entity; Branch Number; Business Date; End Of Day Indicator; Transaction Type Indicators; Transaction Count; Transaction Dollar Amount; Discrepancy Indicator; Confirmation Number; Confirmation Time; Session Number; Teller ID Number; and the MICR line data captured at the teller station.

As depicted in FIG. 4, an Import module 165 of the present invention is located at the back office 170. The Import component 165 processes transactions from the Transaction Journal 160 which it reads throughout the course of the day. The Import component 165 is invoked at the start of each business day and executes (performs the read operation) periodically throughout the day (e.g., every 15 minutes) in order to pick up new transactions. The import module 165 examines each transaction that has been imported and invokes the appropriate back office 170 components that are required to process the transaction.

Each transaction imported during a given import run is examined to determine the type of the transaction. If the transaction is a Financial transaction, as described above, the record for that transaction is stored in the Transaction Repository 175. If the transaction is for archive purposes only (e.g., Group 1 transactions) the transaction is passed to an Archive Cross Reference Builder component 180 (see FIG. 10). If the transaction reflects a Work In Progress transaction, the transaction is passed to a Work In Progress component 185. Branch Confirmation transactions are passed to an End Of Day Confirmation component 190. Finally, if the transaction is an All Items Only transaction (e.g., a non paper transaction) it is stored in the Transaction Repository 175.

The Import component 165 is invoked at the start of each business day either by the System Manager 195, or by another means of job scheduling. Subsequent import runs are invoked automatically (e.g., every 15 minutes). The System Manager 195 provides an On-line means of invoking the daily start-up of the Import process. The System Manager 195 further allows the operator to monitor and control the Import process by viewing the result of each import run. The System manager 195 also allows monitoring and control the End of Day Confirmation process between the back office. 170 and the Retail mainframe 155, and provides for the management of system exception conditions which may occur within the back office 170. Back office processing exception conditions are stored in a system journal (not shown) and can be viewed via a System Manager 195 screen. Exception conditions are detected by each component of the back office platform 170 and are recorded in the system journal. The System manager 195 also allows for viewing of Work In Progress Batches that have been "cut" by a given teller (as described below). The files required to view this data are created by the Work In Progress component 185.

Figure 5:
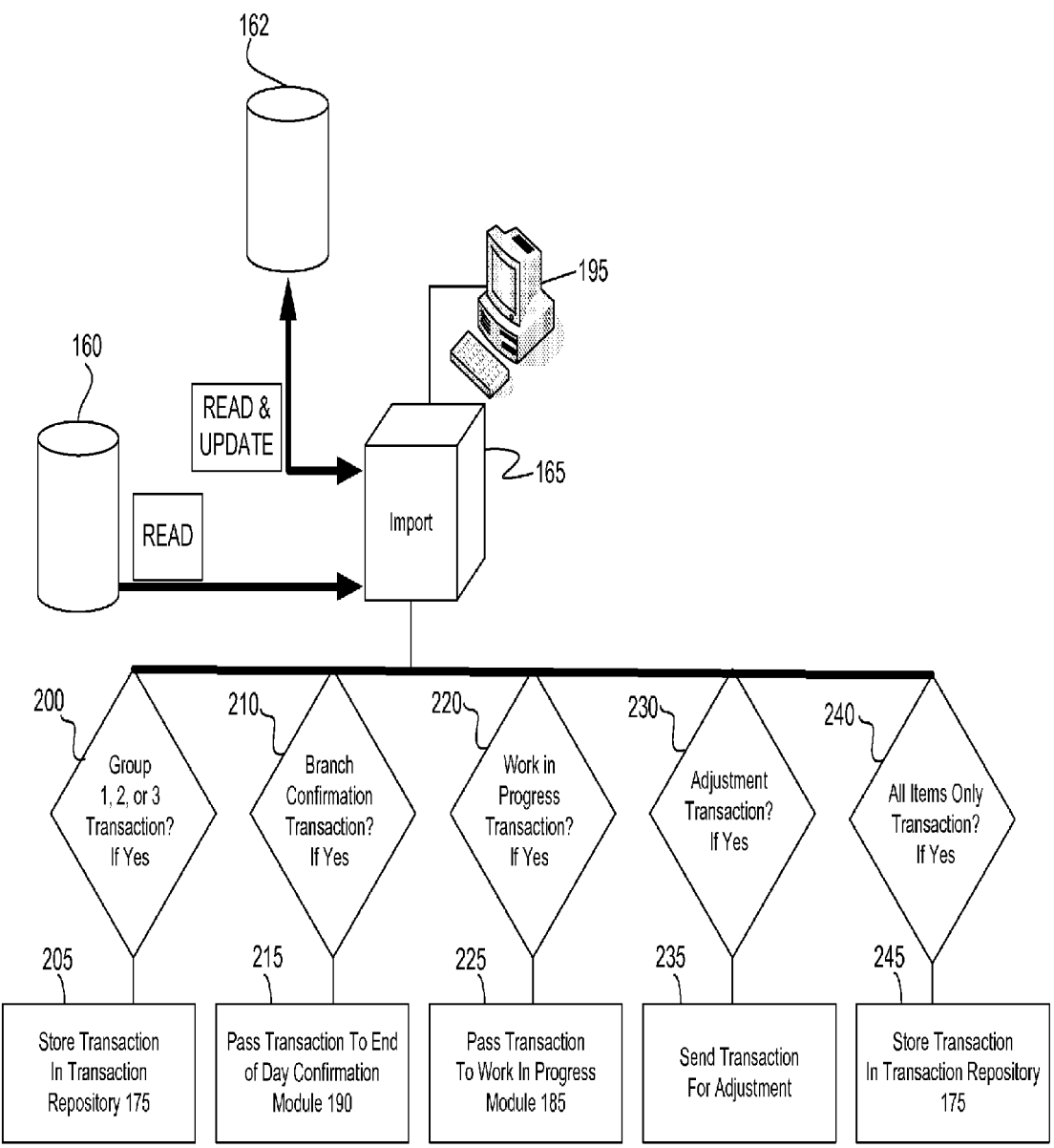
FIG. 5 illustrates the process conducted by the Import module.

FIG. 5 illustrates the process conducted by the Import module 165. As previously described, the import module 165 is invoked at the beginning of the day and is periodically invoked (e.g., every fifteen minutes) in order to pick up new transactions. For each record in the Transaction Journal 160, Import 165 tests to see what should be done with the record in steps 200, 210, 220, 230 and 240. If the answer to any of the tests is NO, the testing of the transaction goes onto the next test. Import 165 uses a control file 162 in order to keep track of the status and progress of the transaction processing and to store control parameters. As previously described, the System Manager 195 is used to invoke and monitor the import process.

In step 200 it is determined if the transaction is a Group 1, 2 or 3 transaction. If the transaction is a Group 1, 2 or 3 type transaction, the transaction is stored in the Transaction Repository 175. In step 210 it is determined if the transaction is a branch confirmation transaction (e.g., end of day totals). If the transaction is a branch confirmation, the confirmation is passed onto the End of Day Confirmation module 190. If the transaction is a Work in Progress transaction (step 220) the transaction is passed onto the Work in Progress module 185 (step 225). If the transaction is an adjustment transaction (step 230) the transaction is passed onto an Adjustment module (step 235). Adjustment transactions are entered by a teller to correct a previously submitted transaction. The adjustment to the original transaction can be done either manually by an operator or automatically by the system. Finally, if the transaction is an All Items Only transaction (step 240) the transaction is stored in the Transaction Repository 175 (step 245).

The Transaction Repository 160 is one of the key elements of the system and method of the present invention. As previously described, electronic data concerning transactions which was previously captured at the back office 170 using expensive, time consuming and error prone processes and equipment is now captured by the tellers at the time of the transaction, imported and stored in the Transaction Repository 160. The Transaction Repository 160 provides the primary data storage, indexing, and retrieval services for the present invention. This Repository 160 provides for concurrent data storage, indexing, and retrieval by the other modules and processes described herein.

Each transaction resident in the Transaction Repository 160 is indexed at least by the MICR data provided by the teller MICR swiping process. The transactions are preferably further indexed by the Branch, Teller and Batch (group 1, 2 or 3) in order that the other modules of the system can quickly locate and access the transaction data. As previously described, transactions are passed from Import 165 via an application program interface (API) to the Transaction Repository 175. The transactions stored in the Transaction Repository 175 include: Financial transactions (Group 2 Deposit Tickets and associated checks and Group 3 payment, sales, or cashed checks, that have been MICR Swiped by the Teller); Archive Only transactions (Group 1 transactions); and All Items Only transaction (non paper transactions).

Figure 6:
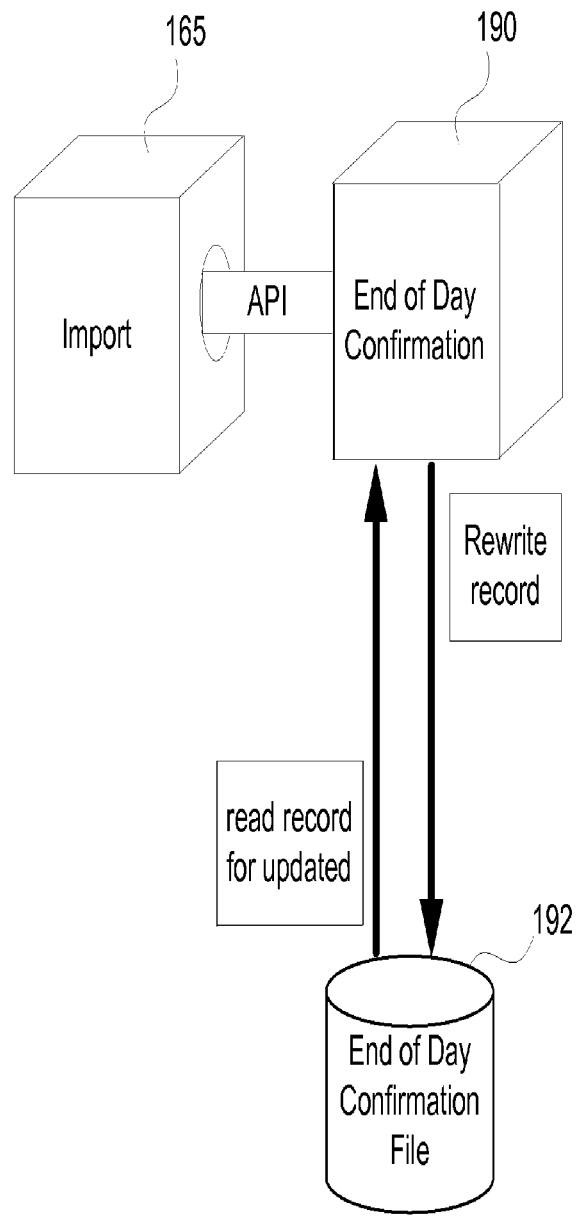
FIG. 6 illustrates the detail of the End of Day Confirmation module and associated processes.

FIG. 6 illustrates in more detail the End of Day Confirmation module 190 and associated processes. The primary purpose of the End of Day Confirmation module 190 is to confirm, at end of the branch day, the completeness of the data feed from the branches 150 to the back office 170 through the Transaction Journal file 160 (see FIG. 4). As depicted in FIG. 6, the End of Day Confirmation module 190 maintains an End of Day Confirmation File 192. This file 192 contains at least one record for each branch 150 of the bank. Each of these branch records contain accumulators which keep track of the financial totals processed by the branch during the course of the entire day. The accumulators are organized by the transaction types (e.g., cash only deposits).

As transactions are received by Import 165, the transactions are passed to the End of Day Confirmation module 190. The End of Day Confirmation module 190 reads the branch from the transaction record and uses this information to retrieve the branch record from the End of Day Confirmation File 192. The dollar amount related to the transaction is then aggregated within the branch record with respect to the transaction code type.

At the end of day in each branch, Confirmation transactions are passed to the End of Day Confirmation component 190 from the Import component 165. There are confirmation-transactions for each transaction code type for each branch. The confirmation process in the End of Day Confirmation component 190 matches transaction code values to ensure that all work has been successfully received by the back office 170. This is accomplished by comparing the values in the received Confirmation transactions with the values accumulated throughout the day in the branch records contained in the End of Day Confirmation File 192.

If the confirmation process fails for a given branch, this failure is displayed on the System Manager 195 screen. This notification provides an early warning to the back office personnel that a potential problem exists in the teller, branch or back office systems.

Figure 7:
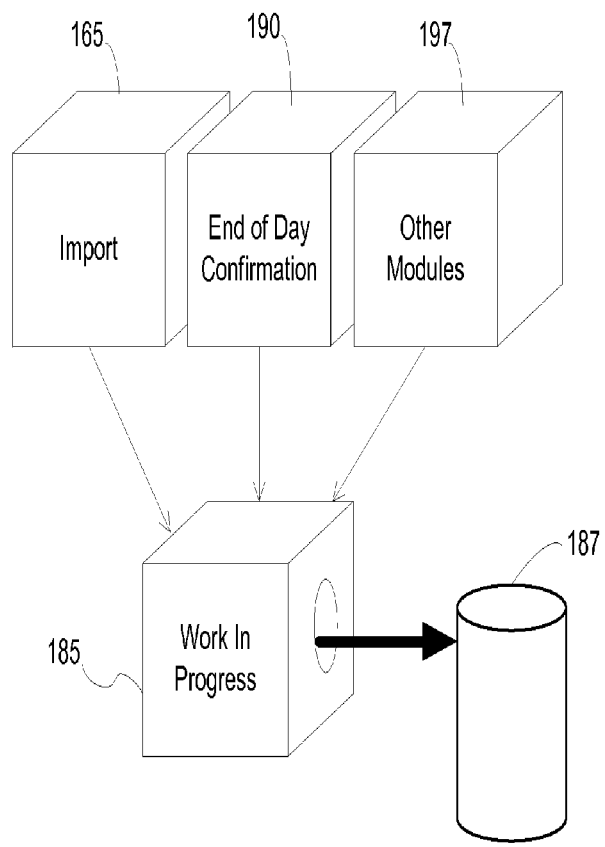
FIG. 7 illustrates the detail the Work In Progress component.

FIG. 7 illustrates in more detail the Work In Progress component 185 of the present invention. A work in progress consists of one or more "live" transactions which have not been completely processed. The primary function of this component 185 is to write Work In Progress transactions to a Work In Progress data set 187 as the transactions are received by the back office 170. The purpose of this function is to enable the tracking of these transactions as they proceed through the various processing steps and stations at the back office 170. The Work In Progress data set 187 is a repository where units (batches) of Work in Progress are recorded. Although not shown in FIG. 7, the Work In Progress data set 187 is accessible by the System Manager 195 for monitoring and tracking of Work In Progress transactions.

As illustrated in FIG. 7, Work In Progress transactions are fed to the Work In Progress component 185 by both the Import component 165 and the End of Day Confirmation module 190. Additionally, sensors can be placed throughout the back office 170 and the branches 150 (see FIG. 4) in order for these components to report the location and progress of a Work In Progress. These sensors are generically represented in FIG. 7 as Other Modules 197. For example, the physical paper arrives at the receiving office of the back office 170 from a branch 150, an operator scans the control card (115, FIG. 3) on top of the batch. This sensor feeds the control information for the batch to the Work In Progress module 185 for inclusion in the Work In Progress database 187. Similarly, as the batch is fed into the sorter (not shown), a sensor in the sorter reads the control card 155 and informs the Work In Progress module 185 which updates the record for the batch in the Work In Progress database 187. By this means, the system is able to track the location and progress of the transactions as they pass through the back office 170.

Figure 8:
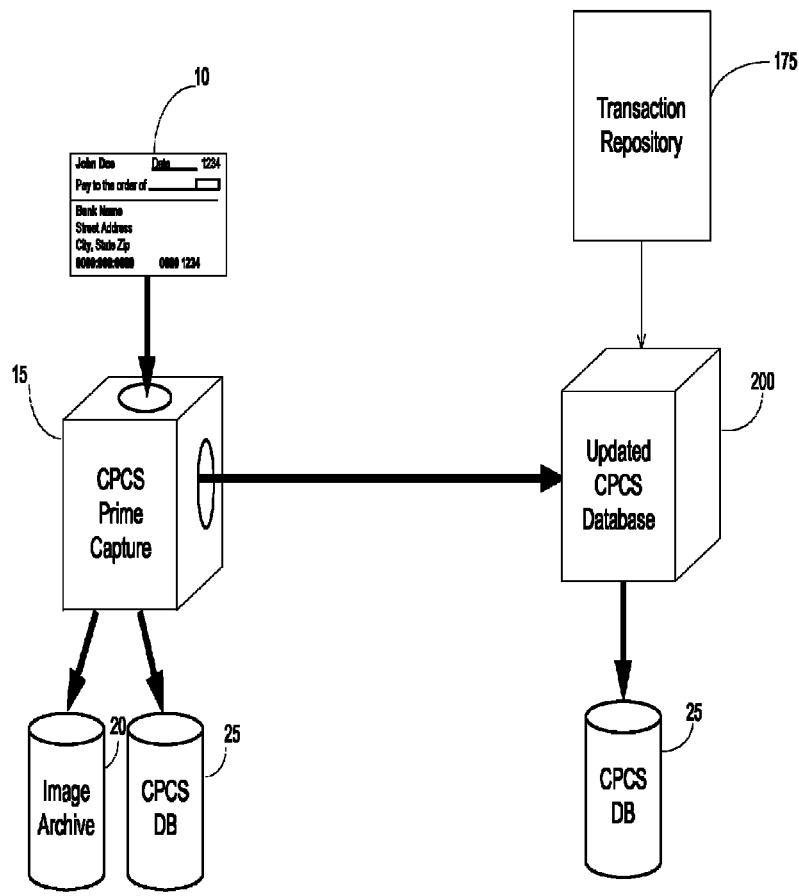
FIG. 8 depicts an overview of the process of linking the electronic transactions in the Transaction Repository 175 with the data captured by the CPCS Prime Capture process.

The power of the present invention is readily apparent once all of the paper 10 representing all of the transactions processed throughout the day at the branches 150 arrives at the back office 170 from the branches 150. FIG. 8 depicts an overview of the process of linking the electronic representations of the transactions contained in the Transaction Repository 175 with the data in the Image Archive 20 and the CPCS database 25 generated by the CPCS Prime Capture process 15.

Figure 1:
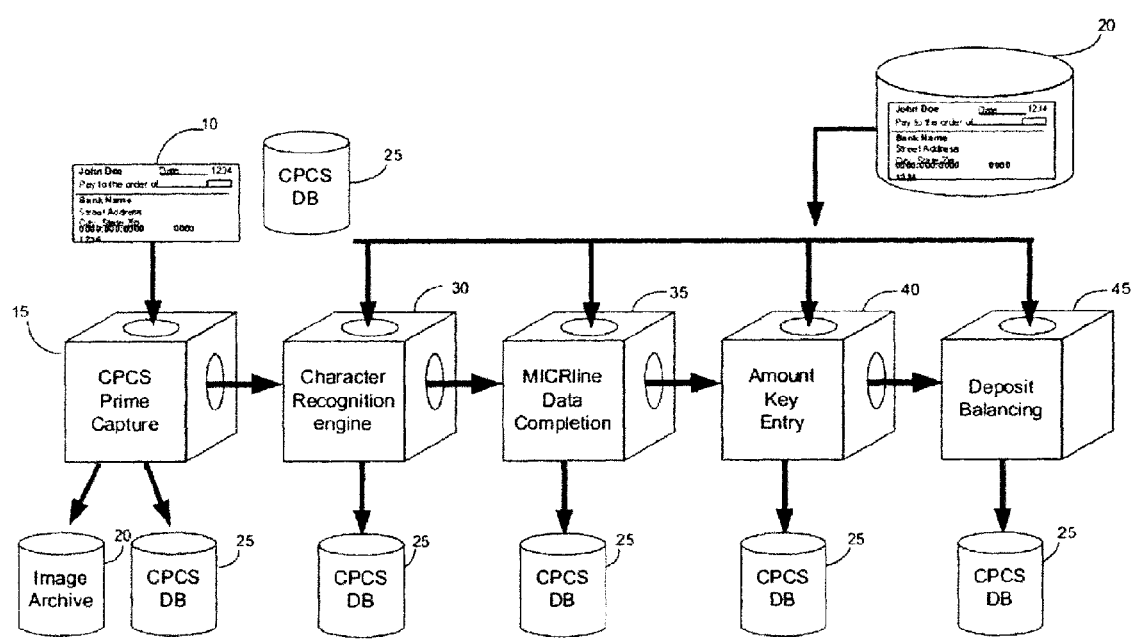
FIG. 1 illustrates the back office processing of the prior art.

As previously described with respect to the prior art system of FIG. 1, the first process undertaken at the back office 170 of the present invention is to capture both images of the paper 10 (front and back) and the MICR data contained on the paper 10. As with the prior art, CPCS Prime Capture 15 accomplishes both of these functions using conventional image enabled sorters, optical readers and MICR readers. The image data of the two sides of each of the papers 10 is stored in an image archive database 20, while the MICR data read from the paper is stored in a CPCS database 25. This is where the similarity to the prior art systems and methods ends. As previously described, the prior art system of FIG. 1 employed: a Character Recognition Engine 30 to analyze the captured images in order to determine the amount of the transaction; a MICRline Data Completion module to [NOTE to inventors, what does (did) this module de]; and if either of the automated processes failed to capture the amount of the transaction, an operator would have had to manually read the image of the check from the image database 20 and input the amount into the transaction record contained in the CPCS database (module 40).

In direct contrast to the systems and method of the prior art, the present invention uses an automated Update component 200 which is used to link the data electronically captured by the teller and contained in the Transaction Repository 175 with the data contained in both the Image Archive 20 and the CPCS database 25. In general, the Update component 200 extracts the relevant information (e.g., dollar amount or account number) related to a transaction from the Transaction Repository 175 and inserts this information into the record from paper 10 associated with the transaction contained in the CPCS database 25. The CPCS database 25 already has a pointer to the image of the paper 10 in the Image Archive 20. In this manner, all of the relevant information regarding transactions is gathered and is easily accessible without the expensive and time consuming, processes and equipment of the prior art.

As described above, the primary function of the Update component 200 is to obtain transaction specific data from the Transaction Repository 175 following the completion of a CPCS Prime Pass Capture 15 run. Update module 200 updates the CPCS database 25 with dollar amounts for checks, account numbers for Counter Deposit Tickets, and Cash In/Out Amount for mixed deposits. As previously described, the data for the transaction contained in the Transaction Repository 175 is generated at the teller workstation at the branch 150. In contrast, in the prior art, this type of data was either manually entered by a clerk at the back office 170 or was attempted to be captured by the imaging system. As described above, both of the prior art systems were error prone and very labor intensive. As the teller is able to swipe the documents and enter the financial data at a more deliberate pace, the likelihood that errors would occur during the use of the present invention are. Furthermore, as the teller is directly responsible for the integrity of each financial transaction he or she processes the teller presumptively double checks each transaction. As this verification by the teller occurs "offline" with respect to the back office processing, the speed of the back office processing is greatly enhanced. Finally, the teller system includes an automatic proofing function which electronically catches errors (e.g. in deposit slip or check amount entry) by the teller before, they enter the system.

Update component 200 is invoked after the completion of a CPCS Prime Pass Capture 15 on branch work (i.e., physical paper 10 of Group Types 1, 2 and 3). The paper 10 associated with Group 2 & 3 type transactions is captured throughout the course of the evening and paper related to Group 1 type transactions are captured at end of day. The output of the CPCS Prime Pass Capture 15 is a string which contains records for all of the paper associated with the transactions processed during the run. The string is stored in the CPCS database 25.

Figure 9:
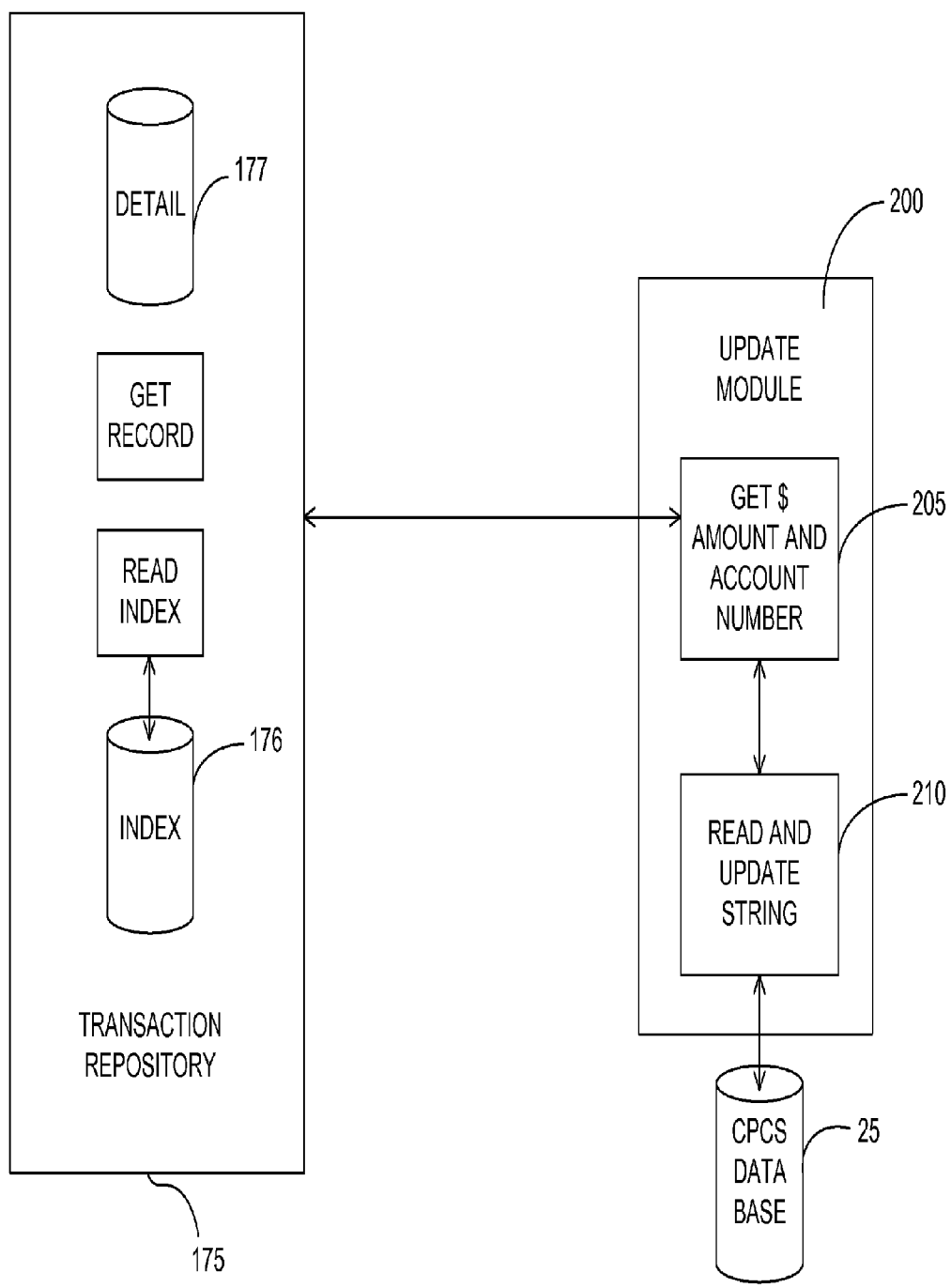
FIG. 9 illustrates the process conducted by the Update component.

FIG. 9 illustrates the process conducted by the Update component 200 after completion of the CPCS Prime Pass Capture 15. The first operation is that a Read and Update module 210 of the Update component 200 opens the string stored in the CPCS database 25 in order to read the transactions. The transactions are then read one by one. When a Group 1, 2 or 3 type transaction is encountered on the string, the Read and Update module 210 reads from the siring the MICR data for the transaction. After the Read and Update module 210 has read the MICR data for the transaction from the string in the CPCS database 25, a Get module 205 of the Update component 200 accesses the Transaction Repository 175 using the MICR data as an index to search the Transaction Repository 175. As depicted in FIG. 9, the Transaction Repository 175 is comprised of an Index 176 and a Detail database 177. As previously described, the transactions stored in the Transaction Repository 175 are indexed in several ways in order to ease the access of the detailed transaction data. These various indexes are stored in the Index database 176 while the complete record for the transaction is stored in the Detail database 177. The MICR data is used as an index key to search the Index database 176 which is then used to retrieve the transaction specific data (e.g., dollar amount for a check, account number for a counter deposit ticket, or Cash In/Out amount for a mixed deposit) from the Detail database 177.

The Transaction Repository 175 returns the retrieved transaction data to the Get module 205 which passes the data onto the Read and Update module 210. The Read and Update module 210 then updates the transaction data contained in the string in the CPCS dataset 25 with the retrieved data (e.g., the check dollar amount). For Counter Deposit Tickets, the dollar amount and account number are inserted into the CPCS string. For deposits with Cash In/Out, a Cash In/Out transaction will be inserted into the CPCS string.

After the Update component 200 has read all of the transactions from the string, retrieved all of the data from the Transaction Repository 175 and updated the string, the Update component 200 passes to the Work In Progress component 185 (FIG. 7) an electronic list of all work in progress batch numbers present on the string in order to track the progress of the transactions.

Figure 10:
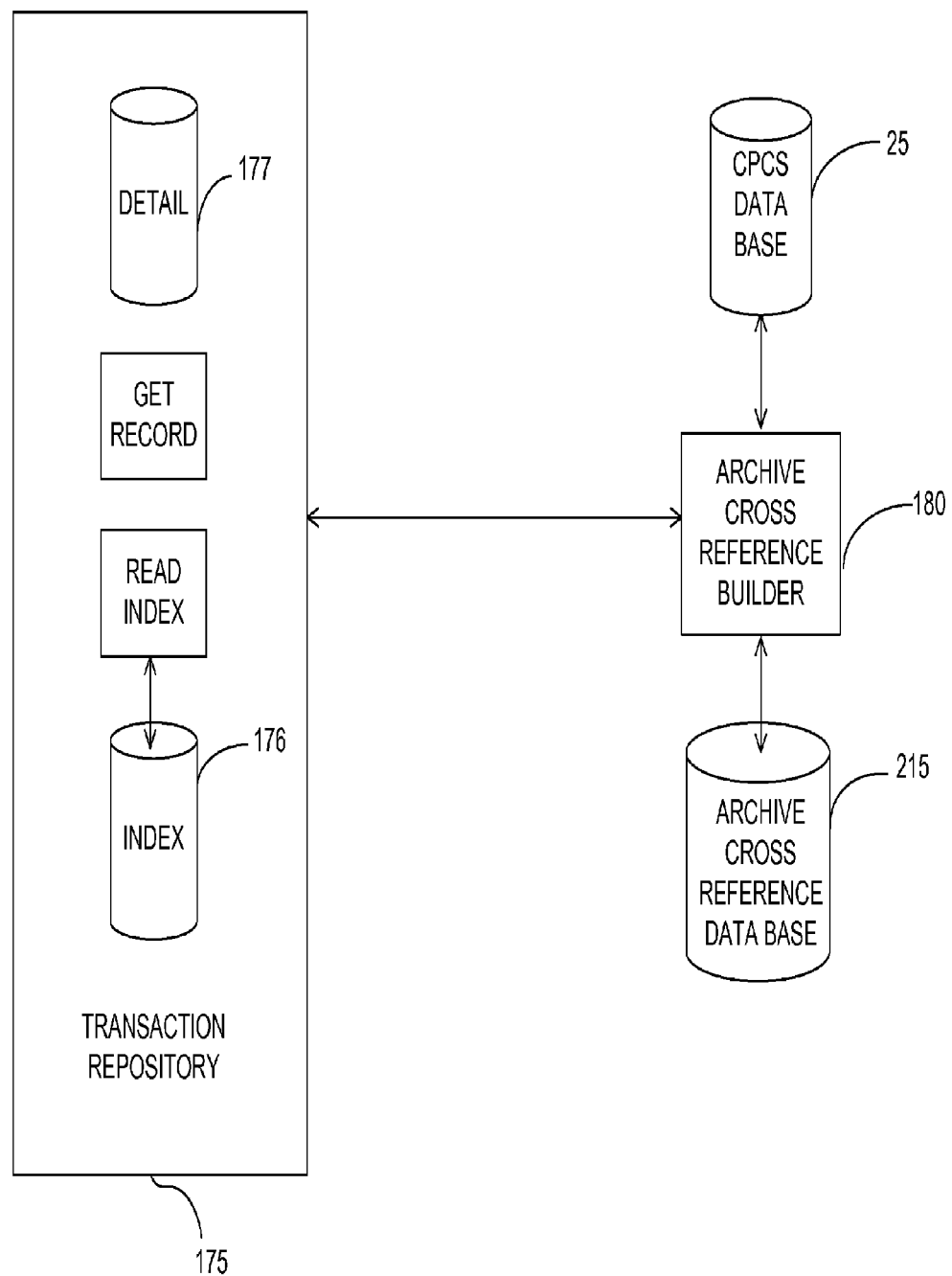
FIG. 10 depicts the process by which the Archive Cross Reference. Builder creates an Archive Cross Reference database.

Group 1 transactions, credits and debits with cash, check or credit offsets and cash only deposits require special processing in order to track these transactions. As previously described, Group 1 transactions are no longer considered "live" as the financial aspect of the transactions has been completed at the teller work station. As such, Group 1 transactions are treated differently than Group 2 or 3 transactions which require financial processing. FIG. 10 illustrates the process by which the Archive Cross Reference Builder 180 creates an Archive Cross Reference database 215. The primary function of the Archive Cross Reference Builder 180 is to create the electronic Archive Cross Reference file 215 for transactions in Group 1, Archive Only in order to create the connection between the representation of the Group 1 financial transactions represented by the records in the Transactions Repository 175 and the records for the transactions contained in the CPCS dataset 25. As an alternative to the Archive Cross Reference Builder 180, the Update module 200 could perform this cross reference function. It is preferred though, to have the separate Archive Cross Reference Builder 180 perform the cross referencing as this function can be performed out the critical path of the Update module 200 which is also processing the "live" financial transactions of Groups 2 and 3.

The physical documents associated with on-line transactions (Group 1) created at the teller workstation 55 (FIG. 2) are delivered to the back office 170 where the MICR and image data is captured by the CPCS Prime Pass Capture component 15 as described above with respect to FIG. 8. The string containing the transactions resulting from the CPCS Prime Pass Capture 15 run is stored in the CPCS database 25. Similar to the process described above with respect to the Update component (FIG. 9) the Archive Cross Reference Builder 180 uses the MICR data as an index to search the Transaction Repository 175. The MICR data is used as an index key to search the Index database 176 which is then used to retrieve the transaction specific data (e.g., dollar amount) from the Detail database 177. With the electronic transaction information from the Transaction Repository 175 and the captured transaction information from the CPCS database 25, the Archive Cross Reference Builder 180 generates a cross reference record which is written to the Archive Cross Reference file 215. In a preferred embodiment of the present invention the cross reference comprises pointers to the appropriate records in the CPCS database and the Transaction Repository. The Archive Cross Reference file 215 is used by the conventional back office processes such as research and adjustment programs.

Figure 11:
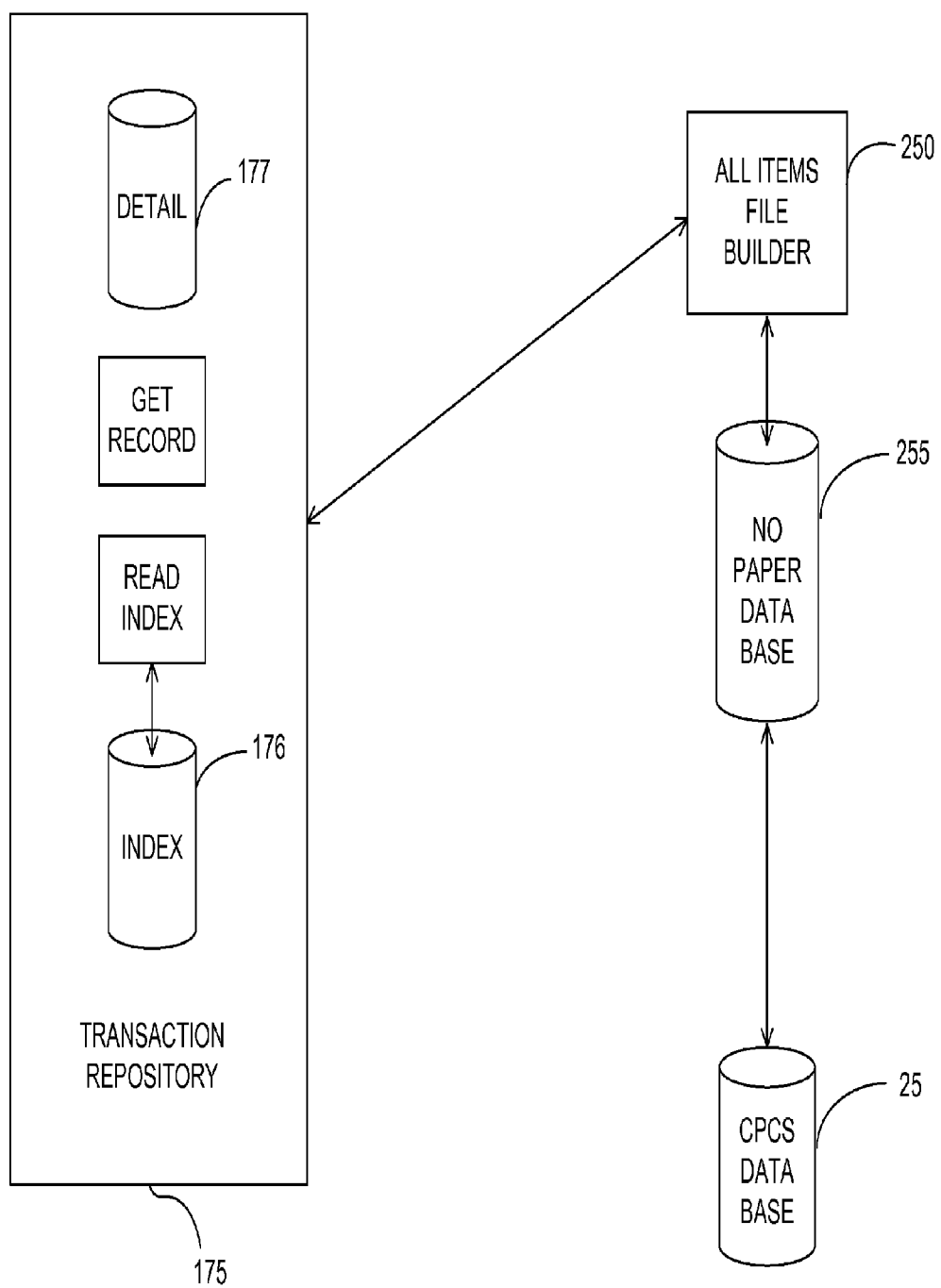
FIG. 11 depicts the process performed by the All Items File Builder.

Not all of the transactions conducted by the teller generate paper documentation which is sent to the back office 170. Accordingly, the present invention provides an All Items File Builder 250 as depicted in FIG. 11 in order to record these paperless, transactions. As previously described, all of the transactions are electronically captured at the teller workstation 55 (FIG. 2) and are populated into the Transaction Repository 175. The ultimate function of the All Items File Builder 250 is to pass the electronic data regarding paperless transactions to the conventional back office processes (e.g., research and adjustment platforms).

The All Items File Builder 250 requests from the Transaction Repository 175 all of the transactions which are electronic, no paper transactions. The Transaction Repository is able to identify and extract these records and pass them back to the All Items File Builder 250. Each of these records is written to a No Paper database 255. Each of the records is read from the No Paper database 255 by another module (not shown) and the records are then used to create new records in the CPCS database 25 which had previously only contained records for transactions captured by the CPCS Prime Pass Capture 15 (FIG. 8). The CPCS database 25 now has a complete set of data relating to all of the transaction processed at the branches throughout the day.

Figure 12:
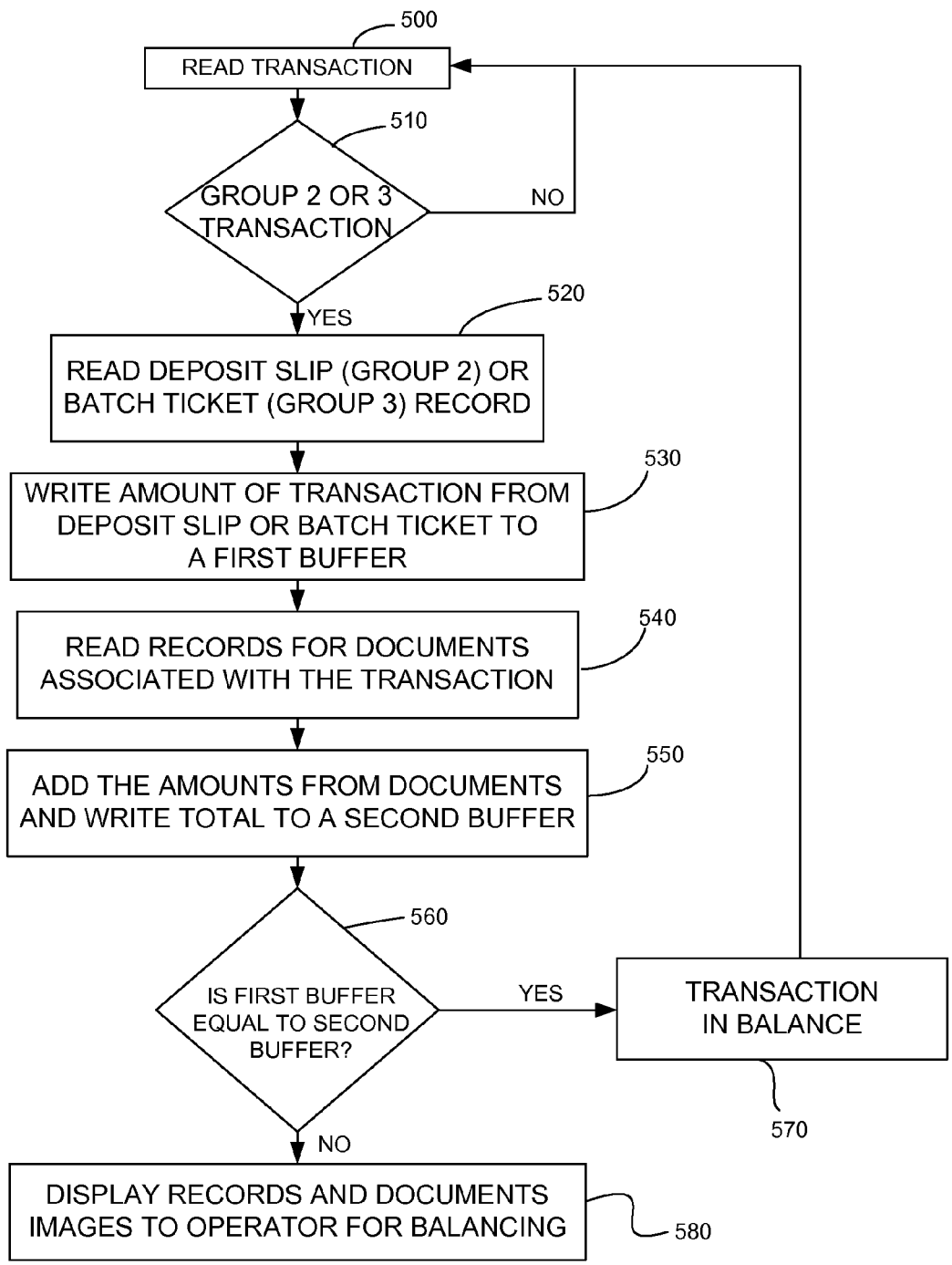
FIG. 12 illustrates the deposit balancing procedure.

FIG. 12 illustrates the Deposit balancing function as implemented in the present invention. The process of Deposit balancing in the present invention is essentially the same as described above with respect to the prior art of FIG. 1. One big difference is that because of the data entry by the teller and inclusion of this data in the CPCS dataset (by Update module 200, FIG. 9) a drastically reduced number of deposit transactions will not be automatically balanced by the system. Accordingly, fewer deposit transactions will require manual balancing by an operator. A further improvement of the present invention is the case of missing documents, the teller data contained in the Transaction Repository 175 can be used to supplement the data scanned from the physical documents (contained in CPCS database 25, FIG. 8).

In step 500 in FIG. 12, a record or a group of records comprising a transaction is read from the CPCS database 25 (FIG. 8). Use of the data from the CPCS database 25 is preferred to balancing from the teller data found in the Transaction Repository 175 (FIG. 4) as this serves as a double check of the balancing performed by the teller at the teller's workstation. In step 510 it is tested whether or not the transaction is a Group 2 or 3 transaction. If the transaction is not a Group 2 or 3 type (i.e., it is a Group 1 transaction), the next transaction is read (step 500) from the Transaction Repository 175. Group 1 transactions do not require balancing as the financial aspect of the Group 1 transactions is complete at the teller's workstation.

If the transaction is either a Group 2 or 3 type transaction, the deposit slip (for Group 2) or batch ticket (for Group 3) record is read for the transaction (step 520). The amount of the transaction is read from the deposit slip or batch ticket record and written to a first temporary buffer (step 530). In step 540 the records for each of the documents (e.g., checks) which are associated with the deposit slip or batch ticket for the transaction are read. The dollar amounts of all of the documents in the transaction are summed in step 500 and the total is written to a second temporary buffer. In step 560, the first and second buffers are compared to verify that the transaction is in balance. If the two buffers are equal, the transaction is balanced (step 570) and the process (steps 500, 510, 520, 530, 540, 550, 560, and 570) is repeated for the next transaction.

If the two buffers are not equal, the deposit is out of balance and requires human intervention. In step 580 the records for the transaction from the Transaction Repository 175 and the CPCS database 25, and the images of the documents representing the transaction (from the image database 20, FIG. 8)

are displayed to an operator. Given all of this information on a single workstation/display screen, the operator is then able to determine why the deposit did not balance.

If a record for a document is missing from the CPCS database 25 and from the image database 20, but a record exists in the Transaction Repository, the operator performing the balancing has the option of accepting the dollar amount which appears from the Transaction Repository 175 and approving the balancing. In this case, the document could be missing, for example, if the document was misfiled with a different batch or was not read properly by the CPCS prime pass operation (e.g., was physically behind a different document). Alternatively, the system itself may balance an out of balance transaction under certain conditions (e.g., one check is missing, and the record for that check in the Transaction Repository 175 indicates the amount of the check is below a threshold amount (e.g., $100)).

While the operator is investigating out of balance transactions, the process steps 500, 510, 520, 530, 540, 550, 560, and 570 run in parallel on the remaining of unprocessed transactions in the transaction repository. Out of balance transactions may be buffered for processing by the operator.

As previously described, the system and method of the present invention provides significant advantages over the prior art processing methods and systems. Less manual labor and less expensive equipment is required to implement and run the system of the present invention. The present invention experiences a significant reduction in errors associated with both the character recognition process and the manual processes of the prior art. Although the teller is electronically capturing more data than in the past, the present invention simplifies the teller process due to far fewer sorts of the physical paper associated with the transactions. The system and method of the present invention enables a more constant flow of work from the branches to the back office which in part results in extended customer hours for centralized Automated Teller Machines (ATM) and branch processing due to freed capacity at the back office. The present invention all but eliminates the end of day proofing previously performed by tellers is all but eliminated.

The system of the present invention provides for easy identification of missing papers and enhances the return items process for the bank. Using the present invention, accurate assignment of the float for cashed checks is enabled. The system reduces the number of "on-us" financial control documents (e.g., General ledger tickets, Cash-in, Cash-out). The system further improves the cash reconciliation process based upon earlier access to the document images.

Although the present invention has been described in relation to particular embodiments thereof, many other variations and other uses will be apparent to those skilled in the art. It is preferred, therefore, that the present invention be limited not by the specific disclosure herein, but only by the gist and scope of the disclosure.

We claim:

1. A computer-implemented system for processing banking transactions including paper documents, the system comprising:

at least one branch host computing system having a branch host computer processor; and a back office computing system having a back office computer processor, the back office computing system and branch host computing system connected over a network, wherein the branch host computer processor and the back office computer processor are programmed to collectively perform steps including:

capturing first transaction data electronically from at least one paper document associated with each transaction, the first transaction data including at least magnetic ink character recognition data and an amount of each transaction, captured electronically during banking transactions conducted at a point of contact associated with a branch location;

storing the first transaction data in a transaction file at the branch host computing system;

reading the first transaction data from the transaction file;

forwarding the at least one paper document associated with each of the banking transactions conducted at the point of contact to the back office computing system;

generating second transaction data reflecting information associated with the at least one forwarded paper document for each transaction, wherein generating the second transaction data comprises the step of imaging the at least one forwarded paper document associated with each transaction;

linking the first and second transaction data with respect to a common financial transaction; and processing the first and second transaction data to complete the banking transactions, the processing of the first and second transaction data not including magnetic ink character recognition line data completion and amount key entry unless an exception item is detected during the processing of the first and second transaction data.

2. The system according to claim 1, wherein the point of contact comprises a bank branch location, the system further transmitting the transaction file to a different location.

3. The system according to claim 1, further including a plurality of bank branch locations, wherein capture and storage steps are performed at each of the bank branch locations, wherein there is a separate transaction file for each bank branch location.

4. The system according to claim 3, wherein the system consolidates the transaction data from the transaction files from each of the bank branch locations into a consolidated transaction file, wherein the reading is performed on the consolidated transaction file.

5. The system according to claim 4, wherein the consolidation step occurs several times during a business day.

6. The system according to claim 5, wherein the system further performs the step of electronically transmitting the transaction files from each of the bank branch locations to a central location, wherein the step of consolidation occurs at the central location.

7. The system according to claim 6 wherein the reading step occurs at the central location.

8. The system according to claim 6 wherein the system further performs the step of electronically transmitting the consolidated file from the central location to a different location, wherein the linking step occurs at the different location.

9. The system according to claim 8 wherein the central location is a retail bank central location and wherein the different location is a back office processing location.

10. The system according to claim 4, wherein the consolidating step further comprises the step of consolidating less than all of the transaction data from each of the transaction files into the consolidated file.

11. The system according to claim 1 wherein the transaction data in the transaction file reflects less than all of the banking transactions conducted at the point of contact.

12. The system as set forth in claim 1, further comprising the step of:

updating the second transaction data with at least a portion of the first transaction data.

13. The system as set forth in claim 12, wherein the portion of the first transaction data is a dollar amount associated with the financial transaction.

14. The system as set forth in claim 1, wherein the step of generating the second transaction data comprises the step of reading the Magnetic Ink Character Recognition (MICR) data.

15. The system as set forth in claim 1, wherein the system further performs the step of inserting a type identifier into the first transaction data, the type identifier indicating a type of transaction contained in the first transaction data.

16. The system as set forth in claim 1, wherein the back office computing system further performs the step of maintaining, at the back office location, a back office aggregate dollar value of the financial transactions contained in the first transaction data.

17. The system as set forth in claim 16, wherein the system further performs the steps of:
generating an aggregate dollar value of financial transactions conducted at the point of contact;
forwarding the aggregate dollar value to the back office location; and
comparing the aggregate dollar value with the back office aggregate dollar value.

18. The system as set forth in claim 1, wherein the back office computing system further performs the step of account reconciliation processing.

19. The system as set forth in claim 1, further comprising posting of the financial transactions.

20. The system as set forth in claim 1, wherein the back office computing system further performs proof of deposit processing.

21. A computer-implemented system for processing banking transactions including paper documents, the system comprising;
a back office computing system including a back office computer processor, the back office computing system disposed in a back office location; and
at least one branch computing system including at least a memory and at least one computer processor, the at least one computer processor and the back office computer processor programmed to collectively perform steps including:
capturing first transaction data from at least one paper document associated with each transaction, the first transaction data including magnetic ink character recognition data and an amount of each transaction, the first transaction data reflecting transactions processed at a point of contact, wherein there are a plurality of points of contact and capturing the first transaction data further comprises the step of capturing the first transaction data with respect to transactions conducted at the plurality of points of contact;
storing the first transaction data in at least one electronic transaction file in the memory of the at least one computing system;
transmitting the at least one electronic transaction file to a back office computing device in a back office location;
forwarding the at least one paper document associated with each of the transactions conducted at each point of contact to the back office computing device;
reading the first transaction data from the at least one electronic transaction file;
generating, at the back office location, second transaction data reflecting information associated with the at least one forwarded paper document for each transaction, wherein generating the second transaction data comprises the step of imaging the at least one forwarded paper document associated with each transaction;
linking the first and second transaction data with respect to a common transaction; and
performing financial processing with the first and second transaction data, the processing of the first and second transaction data not including magnetic ink character recognition line data completion and amount key entry unless an exception item is detected during the processing of the first and second transaction data.

22. The system as set forth in claim 21, further comprising the step of:
updating the second transaction data with at least a portion of the first transaction data.

23. The system as set forth in claim 21, wherein the portion of the first transaction data is a dollar amount associated with the transaction.

24. The system as set forth in claim 21, wherein the step of generating the second transaction data comprises the step of reading the Magnetic Ink Character Recognition data associated with the data.

25. The system as set forth in claim 21, further comprising the step of inserting a type identifier into the first transaction data, the type identifier indicating a type of transaction contained in the first transaction data.

26. The system as set forth in claim 21, wherein the back office computing system further performs the step of maintaining, at the back office, a back office aggregate dollar value of financial transactions contained in the transaction data.

27. The system as set forth in claim 21, wherein the at least one computer processor is further programmed to perform the steps of:
generating an aggregate dollar value of financial transactions conducted at the point of contact;
forwarding the aggregate dollar value to the back office; and
comparing the aggregate dollar value with the back office aggregate dollar value.

28. A system for processing banking transactions conducted at a point of contact, the system comprising:
a workstation, the workstation electronically capturing first transaction data reflecting transactions processed at a point of contact;
a memory coupled to the workstation, the memory storing the first transaction data in an electronic transaction file; and
a remote processing facility coupled to the memory, the remote processing facility:
receiving the paper documents,
generating second transaction data reflecting information contained on the paper documents,
reading the first transaction data from the electronic transaction file,
linking the first and second transaction data with respect to a common financial transaction, and
performing financial processing using the first and second transaction data.

29. The system according to claim 28, further comprising a plurality of workstations located in at least one bank branch location.

30. The system according to claim 29, wherein the plurality of workstations is located at a plurality of bank branch locations, the system further comprising:
   a plurality of memories, at least one memory coupled to the workstations located at a bank branch location, the remote processing facility being coupled to each of the memories.

31. The system according to claim 30, wherein the remote processing facility is coupled to the memories through a telecommunications line.

32. The system according to claim 30, wherein the remote processing facility is coupled to the memories through a common memory.

33. The system as set forth in claim 28, wherein the remote processing facility includes a system for imaging the paper documents.

34. The system as set forth in claim 33, wherein the remote processing facility includes a Magnetic Ink Character Recognition (MICR) reader.

35. The system as set forth in claim 28, wherein the workstation includes a Magnetic Ink Character Recognition (MICR) reader.

* * * * *